United States Patent

Bürstinghaus et al.

[11] 4,296,108
[45] Oct. 20, 1981

[54] 2,2-DICHLOROCYCLOPROPYL-METHYL-PHOSPHORIC ACID DERIVATIVES

[75] Inventors: Rainer Bürstinghaus, Weinheim-Lützelsachsen; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 166,573

[22] Filed: Jul. 7, 1980

[30] Foreign Application Priority Data

Aug. 24, 1979 [DE] Fed. Rep. of Germany ........ 2934229

[51] Int. Cl.$^3$ .......................... C07F 9/09; C07F 9/165; C01N 57/04
[52] U.S. Cl. ..................... 424/210; 260/940; 260/949; 260/954; 260/958; 424/216; 424/218; 424/225
[58] Field of Search ............... 260/958, 954, 949, 940; 424/210, 216, 218, 224

[56] References Cited

U.S. PATENT DOCUMENTS

| | | | |
|---|---|---|---|
| 2,811,480 | 10/1957 | Norris, Jr. et al. | 167/53 |
| 2,945,054 | 7/1960 | McCall et al. | 260/958 |
| 3,135,780 | 6/1964 | Suzuki et al. | 260/954 |
| 3,636,161 | 1/1972 | Robinson | 260/958 |
| 4,171,357 | 10/1979 | Theobald et al. | 260/958 |

FOREIGN PATENT DOCUMENTS 1050768 2/1959 Fed. Rep. of Germany .
2634587 2/1978 Fed. Rep. of Germany .

Primary Examiner—Anton H. Sutto
Attorney, Agent, or Firm—Keil & Witherspoon

[57] ABSTRACT

2,2-Dichlorocyclopropylmethyl-phosphoric acid derivatives of the formula I

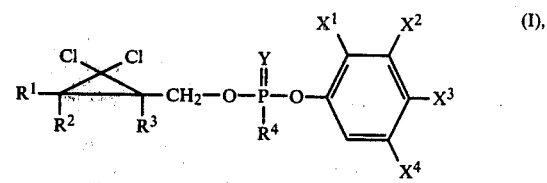

where $R^1$, $R^2$ and $R^3$ are identical or different and are hydrogen or methyl, $R^4$ is unbranched or branched alkoxy of up to 4 carbon atoms, unbranched or branched alkylthio of up to 4 carbon atoms, amino, or alkylamino or dialkylamino, where each alkyl is of up to 5 carbon atoms and is linear or branched, Y is oxygen or sulfur and $X^1$, $X^2$, $X^3$ and $X^4$ are identical or different and each is hydrogen, halogen, nitro, cyano, methyl or methylthio, and their use for controlling pests from the classes of insects, Arachnidae and Nemathelminthes.

6 Claims, No Drawings

2,2-DICHLOROCYCLOPROPYL-METHYL-PHOSPHORIC ACID DERIVATIVES

The present invention relates to 2,2-dichlorocyclopropyl-methyl-phosphoric acid derivatives, pesticides which contain these phosphoric acid derivatives as active ingredients, and a process for combating pests.

German Laid-Open Application DOS No. 2,634,587 discloses S-2,2-dihalo-cyclopropyl-methyl-phosphoric acid derivatives which may be used for controlling insects and nematodes.

We have found that 2,2-dichlorocyclopropylmethyl-phosphoric acid derivatives of the formula I

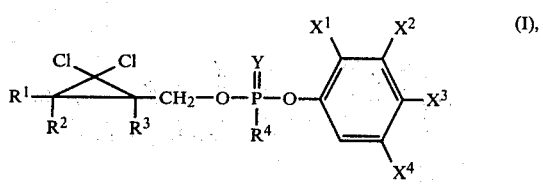

where
  $R^1$, $R^2$ and $R^3$ are identical or different and are hydrogen or methyl,
  $R^4$ is unbranched or branched alkoxy of up to 4 carbon atoms, unbranched or branched alkylthio of up to 4 carbon atoms, amino, or alkylamino or dialkylamino, where each alkyl is of up to 5 carbon atoms and is linear or branched,
  Y is oxygen or sulfur and
  $X_1$, $X_2$, $X_3$ and $X_4$ are identical or different and each is hydrogen, halogen, nitro, cyano, methyl or methylthio, possess a very good insecticidal, acaricidal and nematicidal activity and are superior to known active ingredients of similar structure and of the same type of action.

Examples of linear or branched alkoxy radicals $R^4$ are methoxy, ethoxy, propoxy, isopropoxy and butoxy; examples of alkylthio substituents $R^4$ are methylthio, ethylthio, propylthio, isopropylthio, n-butylthio and isobutylthio; examples of alkylamino and dialkylamino radicals are methylamino, dimethylamino, ethylamino, diethylamino, methylethylamino, isopropylamino, di-n-propylamino, n-butylamino and di-n-butylamino.

Preferred compounds of the formula I are those where $R^1$, $R^2$ and $R^3$ are hydrogen, $R^4$ is methoxy, ethoxy, methylthio, propylthio, isobutylthio, amino, methylamino, dimethylamino or isopropylamino, especially methoxy, Y is oxygen or sulfur and $X^1$, $X^2$, $X^3$ and $X^4$ are hydrogen, nitro or methylthio.

The 2,2-dichlorocyclopropyl-methyl-phosphoric acid derivatives of the formula I may be obtained by reacting a phenol of the formula II, in the presence or absence of an acid acceptor, or by reacting an alkali metal salt, alkaline earth metal salt or unsubstituted or substituted ammonium salt of such a phenol, with a (thio)phosphoric acid diester halide or ester-amide halide of the formula III, in accordance with the following equation:

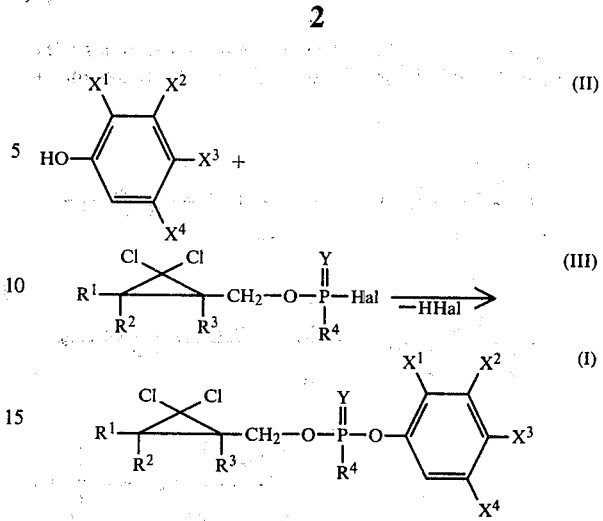

In this equation, $R^1$, $R^2$, $R^3$, $R^4$, $X^1$, $X^2$, $X^3$, $X^4$ and Y have the above meanings and Hal is halogen, preferably chlorine.

The reaction is advantageously carried out in a solvent or diluent which is inert to the reactants. Examples of suitable solvents and diluents are aliphatic and aromatic hydrocarbons and chlorohydrocarbons, eg. petroleum ether, benzene, toluene, xylene, gasoline, methylene chloride, chloroform, carbon tetrachloride and chlorobenzene, ethers, eg. diethyl ether, di-n-butyl ether, methyl tert.-butyl ether, tetrahydrofuran and dioxane, ketones, eg. acetone, methyl ethyl ketone and methyl isopropyl ketone, and nitriles, eg. acetonitrile and propionitrile. Mixtures of these solvents or diluents may also be used.

All conventional acid-binding agents may be used as acid acceptors in the reaction of the phenol of the formula II; alkali metal carbonates and alcoholates, eg. sodium carbonate, potassium carbonate, sodium methylate and ethylate and potassium methylate and ethylate, prove to be particularly suitable, as do aliphatic, aromatic and heterocyclic amines, eg. triethylamine, N,N-dimethylethylamine, trimethylamine, N,N-dimethylaniline, dimethylbenzylamine and pyridine.

Instead of carrying out the reaction in the presence of an acid acceptor, it is equally possible first to prepare a salt of the phenol, for example an alkali metal salt, alkaline earth metal salt, ammonium salt or substituted ammonium salt, preferably an alkali metal salt or ammonium salt, in an undiluted form, and then to react this salt further.

To carry out the process, the starting materials are mostly employed in the equimolar ratio. An excess of one or other reactant can offer advantages in certain cases.

The reaction temperature can be varied within a substantial range. In general, the reaction is carried out at from 0° to 120° C., preferably from 25° to 60° C.

The reaction is in general carried out under atmospheric pressure.

The (thio)phosphoric acid diester halides and ester-amide halides of the formula III, used as starting materials for the preparation of the compounds I, can be prepared from the 2,2-dichlorocyclopropylcarbinols of the formula IV, known from the literature (Acta Chim. Scand., Ser. B, 31 (1977), 463 et seq.) via the 2,2-dichlorocyclopropyl-methyl-(thio)phosphoric acid ester dihalides or amide dihalides of the formula VI, in accordance with the following equations, where the radicals $R^1$, $R^2$, $R^3$, $R^4$, Y and Hal have the above meanings:

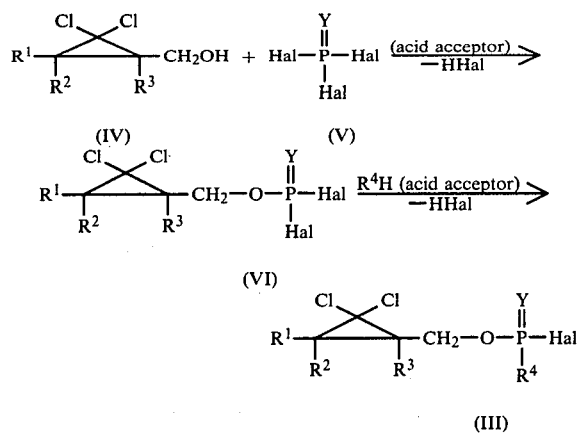

In some cases it can be advantageous to modify the above reaction sequence so that the reaction takes place in accordance with the following equations:

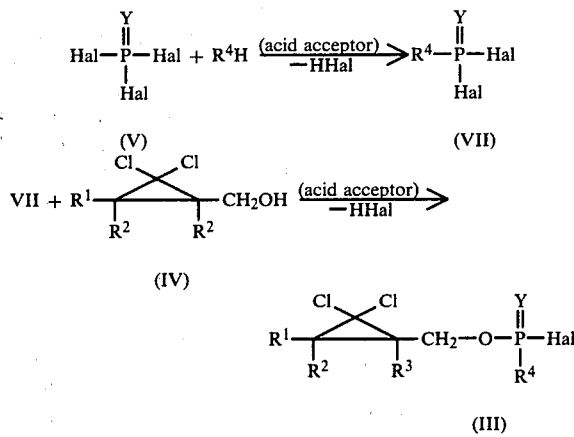

The (thio)phosphoric acid ester dihalides and amide dihalides VI and VII formed as intermediates in the above reaction sequences can either be isolated in an undiluted form or be directly converted to the compounds of the formula III by using a one-vessel process.

To prepare the compounds of the formula III, the reactants shown in the above equations are preferably employed in the equimolar ratio.

For the first reaction stage of each alternative, ie. the reaction of a compound of the formula V with a compound of the formula IV or with a compound of the formula $R^4H$, the reaction temperature may be from $-70°$ C. to $0°$ C., preferably from $-40°$ C. to $-25°$ C. The second stage is, in both alternatives, carried out at from $-50°$ to $+30°$ C., preferably from $-20°$ to $0°$ C.

Both stages of the reaction may, if desired, be carried out in the presence of an organic solvent which is inert to the reactants, for example in an aliphatic or aromatic hydrocarbon or chlorohydrocarbon, eg. pentane, hexane, petroleum ether, toluene, xylene, gasoline, methylene chloride, chloroform, carbon tetrachloride or chlorobenzene, an ether, eg. diethyl ether, methyl tert.-butyl ether, dibutyl ether or tetrahydrofuran, a ketone, eg. acetone, methyl ethyl ketone or methyl isopropyl ketone, or a nitrile, eg. acetonitrile or propionitrile.

Suitable acid acceptors are the acid-binding agents mentioned above in the context of the preparation of the compounds of the formula I. Tertiary aliphatic amines, eg. triethylamine, trimethylamine, N,N-dimethyl-N-ethylamine and heterocyclic amines, eg. pyridine, have proved particularly advantageous.

The compounds of the formula III can also be readily prepared without addition of an acid acceptor if the compound $R^4H$, in the form of an alkali metal salt, is reacted direct with a compound of the formula V or VI.

The Examples which follow illustrate the preparation of the 2,2-dichlorocyclopropyl-methyl-phosphoric acid derivatives of the formula I.

EXAMPLE 1

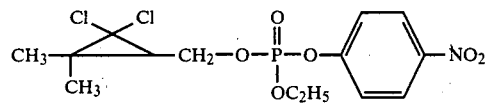

A mixture of 49.9 g of 3,3-dimethyl-2,2-dichloro-1-hydroxymethyl-cyclopropane, 29.8 g of triethylamine and 180 ml of diethyl ether is added dropwise, with stirring, to a solution, cooled to $-30°$ C., of 45.2 g of phosphorus oxychloride in 180 ml of dry diethyl ether. The reaction mixture is stirred for a further 30 minutes at $-10°$ C. and a solution of 13.6 g of ethanol and 9.8 g of triethylamine in 180 ml of ether is then added at the same temperature. The mixture is allowed to come to room temperature in the course of 60 minutes, the triethylamine hydrochloride which has precipitated is filtered off, and the solvent is removed at $10°$ C. under reduced pressure. The residue is taken up in 300 ml of pentane and the insoluble constituent (second liquid phase) is separated off and discarded. The mixture is then again concentrated and the last residues of solvent are removed at room temperature under reduced pressure. 74.5 g of O-ethyl-O-[(2,2-dichloro-3,3-dimethyl-cyclopropyl)-methyl]-phosphoric acid ester chloride are obtained; yield 86% of theory.

$C_8H_{14}Cl_3O_3P$ (296): Calculated: C 32.5; H 4.8; P 10.5. Found: C 32.8; H 5.0; P 10.3.

60 MHz H-NMR spectrum in $CDCl_3$ ($\delta$-values): 1.25 (3H), 1.4 (3H), 1.55 (3H), 1.7 (1H), 4.0–4.6 (4H).

4.17 g of 4-nitrophenol are dissolved in 60 ml of acetonitrile and 6.25 g of finely powdered potassium carbonate are added. 9.29 g of O-ethyl-O-[(2,2-dichloro-3,3-dimethyl-cyclopropyl)-methyl]-phosphoric acid ester chloride are then added dropwise, the mixture is stirred for 2 days at room temperature and the insoluble constituents are filtered off. The filtrate is concentrated in a rotary evaporator, the residue is taken up in 100 ml of diethyl ether and this solution is washed twice with sodium bicarbonate solution and twice with water. After drying the solution over sodium sulfate, the solvent is completely stripped off under reduced pressure, leaving 10.3 g of O-ethyl-O-[(2,2-dichloro-3,3-dimethyl-cyclopropyl)-methyl]-O-(4-nitrophenyl)phosphate in the form of an almost colorless oil; yield: 87% of theory.

EXAMPLE 2

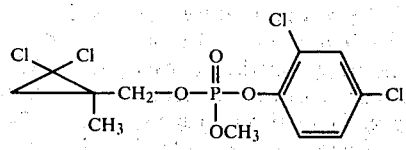

O-Methyl-O-[(2,2-dichloro-1-methyl-cyclopropyl)-methyl]-phosphoric acid ester chloride is prepared, similarly to Example 1, by reacting phosphorus oxychloride with 2,2-dichloro-1-methyl-1-hydroxymethyl-cyclopropane and methanol.

60 MHz H-NMR spectrum in CDCl$_3$ (δ-values): 1.2–1.8 (2H), 1.5 (3H), 3.9 (3H), 4.05–4.5 (2H).

Using the method described in Example 1, 8.46 g of the above phosphoric acid diester chloride, 4.9 g of 2,4-dichlorophenol and 6.25 g of potassium carbonate in 60 ml of acetonitrile give 10.8 g of O-methyl-O-[(2,2-dichloro-1-methyl-cyclopropyl)-methyl]-O-(2,4-dichlorophenyl)phosphate in the form of a colorless oil; yield: 92% of theory.

$C_{12}H_{13}Cl_4O_4P$ (394): Calculated: C 36.6; H 3.3; P 7.9. Found: C 36.9; H 3.2; P 7.7.

60 MHz H-NMR spectrum in CDCl$_3$ (δ-values): 1.15–1.55 (2H), 1.4 (3H), 3.8 (3H), 4.0–4.5 (2H), 6.97–7.45 (3H).

EXAMPLE 3

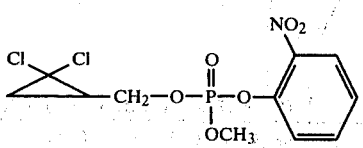

O-Methyl-O-[(2,2-dichloro-cyclopropyl)-methyl]-phosphoric acid ester chloride is prepared, similarly to Example 1, by reacting phosphorus oxychloride with 2,2-dichloro-1-hydroxymethyl-cyclopropane and methanol.

60 MHz H-NMR spectrum in CDCl$_3$ (δ-values): 1.2–2.4 (3H), 3.9 (3H), 3.9–4.5 (2H).

Using the method described in Example 1, 4.78 g of 2-nitrophenol, 5.6 g of sodium carbonate and 9.05 g of the above phosphoric acid diester chloride give 11.1 g of O-methyl-O-[(2,2-dichlorocyclopropyl)-methyl]-O-(2-nitrophenyl)phosphate; yield: 89% of theory.

$C_{11}H_{12}Cl_2NO_6P$ (356): Calculated: C 37.1; H 3.4; N 3.9. Found: C 37.4; H 3.5; N 4.2.

60 MHz H-NMR spectrum in CDCl$_3$ (δ-values): 1.2–2.3 (3H), 3.95 (3H), 4.1–4.6 (2H), 7.1–8.05 (4H).

EXAMPLE 4

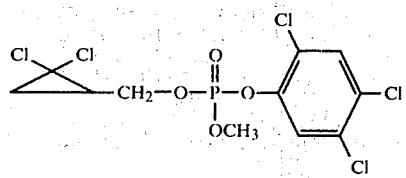

7.3 g of potassium carbonate powder are suspended in a stirred solution of 6.91 g of 2,4,5-trichlorophenol in 70 ml of acetone. 9.05 g of O-methyl-O-[(2,2-dichlorocyclopropyl)-methyl]-phosphoric acid ester chloride are added dropwise, the reaction mixture is heated at 35° C. for 8 hours, and the potassium chloride formed is filtered off. After evaporating off the solvent, the residue is taken up in 150 ml of diethyl ether and the solution is washed three times with sodium carbonate solution and twice with water, and is dried over sodium sulfate. The solvent is then removed under reduced pressure, leaving 13.0 g of O-methyl-O-[(2,2-dichloro-cyclopropyl)-methyl]-O-(2,4,5-trichlorophenyl)phosphate as a syrupy liquid; yield: 90% of theory.

$C_{11}H_{10}Cl_5O_4P$ (415): Calculated: C 31.9; H 2.4; P 7.4. Found: C 32.3; H 2.5; P 7.1.

60 MHz H-NMR spectrum in CDCl$_3$ (δ-values): 1.25–2.3 (3H), 3.95 (3H), 4.05–4.5 (2H), 7.55 (2H).

EXAMPLE 5

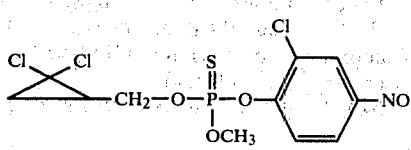

O-Methyl-O-[(2,2-dichloro-cyclopropyl)-methyl]-thiophosphoric acid ester chloride is prepared, similarly to Example 1, by reacting phosphorus sulfide chloride with 2,2-dichloro-1-hydroxymethyl-cyclopropane and methanol.

60 MHz H-NMR spectrum in CDCl$_3$ (δ-values): 1.2–2.46 (3H), 3.85 (3H), 3.9–4.4 (2H).

Using the method described in Example 4, 4.83 g of 2-chloro-4-nitrophenol, 5.2 g of potassium carbonate and 7.5 g of the above thiophosphoric acid O,O-diester chloride, in a solvent mixture of 30 ml of acetonitrile and 40 ml of methylene chloride, give 10 g of O-methyl-O-[(2,2-dichlorocyclopropyl)-methyl]-O-(2-chloro-4-nitrophenyl)phosphorothioate as a pale brown, viscous oil; yield: 89% of theory.

$C_{11}H_{11}Cl_3NO_5PS$ (407): Calculated: C 32.5; H 2.7; N 3.4. Found: C 32.4; H 2.8; N 3.3.

60 MHz H-NMR spectrum in CDCl$_3$ (δ-values): 1.35–2.55 (3H), 4.15 (3H), 4.2–4.8 (2H), 7.7–7.95 (1H), 8.3–8.7 (2H).

EXAMPLE 6

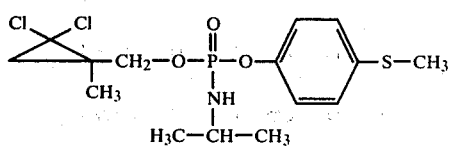

40.05 g of phosphorus oxychloride are introduced into 180 ml of dry diethyl ether; a solution of 46.5 g of 1-methyl-2,2-dichloro-1-hydroxymethyl-cyclopropane and 21.9 g of N,N-dimethylethylamine in 150 ml of diethyl ether is added in the course of 2 hours at −25° C. After all has been added, the mixture is warmed to −10° C. and is stirred at this temperature for one hour. The hydrochloride which has separated out is filtered off and the solvent is evaporated under reduced pressure at 20° C. The oil which remains is taken up in 200 ml of pentane and the resulting solution is kept for 12 hours at −15° C. The mixture is then again filtered, the solvent is stripped off completely (finally at 0.13 mbar and 25° C.) and 73.0 g of O-[(2,2-dichloro-1-methylcyclopropyl)-methyl]-phosphoric acid ester dichloride are obtained; yield: 89% of theory.

60 MHz H-NMR spectrum in CDCl$_3$ (δ-values): 1.3–1.7 (2H), 1.55 (3H), 4.3 (1H), 4.45 (1H).

30 g of the above phosphoric acid ester dichloride are dissolved in 170 ml of diethyl ether, the solution is cooled to −20° C., and a solution of 13 g of isopropylamine in 80 ml of diethyl ether is added dropwise in the course of one hour. The mixture is allowed to come to 15° C. over 3 hours, the hydrochloride which has precipitated is filtered off, and the solvent is removed in a rotary evaporator without exceeding 30° C. The residue is taken up in 120 ml of pentane, the mixture is left to stand overnight in a refrigerator and is then filtered, and the filtrate is concentrated. After completely stripping off the pentane at 25° C./0.13 mbar, the light yellow oil obtained (29.4 g) solidifies to a waxy mass of melting range 34°–43° C. Yield: 90% of theory of O-[(2,2-dichloro-1-methylcyclopropyl)-methyl]-phosphoric acid ester isopropylamide chloride.

C$_8$H$_{15}$Cl$_3$NO$_2$P (295): Calculated: N 4.8. Found: N 4.8.

270 MHz H-NMR spectrum in CDCl$_3$ (δ-values): 1.25 (6H), 1.4 (1H), 1.5 (3H), 1.6 (1H), 3.5 (1H), 4.1–4.45 (2H), 4.4–4.85 (1H).

4.66 g of sodium 4-methylthiophenolate are suspended in a dry solvent mixture of 35 ml of toluene and 20 ml of tetrahydrofuran. 8.5 g of O-[(2,2-dichloro-1-methyl-cyclopropyl)-methyl]-phosphoric acid ester isopropylamide chloride are added dropwise with vigorous stirring, the stirring is then continued for 24 hours at room temperature and thereafter the solvent is stripped off at 50° C. under reduced pressure. The residue is stirred with 150 ml of diethyl ether, the resulting mixture is filtered and the filtrate is washed three times with water. It is then dried over sodium sulfate and concentrated in a rotary evaporator, leaving 10.3 g of an almost colorless solid of melting range 32°–39° C. Yield: 90% of theory of O-[(2,2-dichloro-1-methyl-cyclopropyl)-methyl]-O-(4-methylthiophenyl)-phosphoric acid ester isopropylamide.

C$_{15}$H$_{22}$Cl$_2$NO$_3$PS (398): Calculated: C 45.3; H 5.6; N 3.5. Found: C 45.9; H 5.7; N 3.6.

100 MHz H-NMR spectrum in CDCl$_3$ (δ-values: 1.1–1.25 (6H), 1.3–1.55 (5H), 2.4 (3H), 3.0–3.7 (2H), 3.9–4.4 (2H), 7.15 (4H).

Compounds of the formula I, shown below, are examples of compounds which may be prepared similarly:

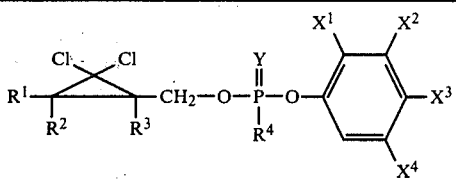

| No. | R$^1$ | R$^2$ | R$^3$ | R$^4$ | Y | X$^1$ | X$^2$ | X$^3$ | X$^4$ | H—NMR data (MHz, solvent, δ-values) |
|---|---|---|---|---|---|---|---|---|---|---|
| 7 | CH$_3$ | CH$_3$ | H | OCH$_3$ | O | H | H | NO$_2$ | H | (60, CDCl$_3$) 1.3 (3H), 1.4 (3H), 1.65 (1H), 3.9 (3H), 4.3 (2H), 7.35 (2H), 8.2 (2H) |
| 8 | CH$_3$ | CH$_3$ | H | OC$_2$H$_5$ | O | Cl | H | Cl | H | (60, CDCl$_3$) 1.25 (3H), 1.35 (6H), 1.65 (1H), 4.0–4.6 (4H), 7.05–7.6 (3H) |
| 9 | CH$_3$ | CH$_3$ | H | OCH$_3$ | O | Cl | H | Cl | Cl | (60, CDCl$_3$) 1.25 (3H), 1.35 (3H), 1.65 (1H), 3.9 (3H), 4.0–4.6 (2H), 7.50 (1H), 7.55 (1H) |
| 10 | H | H | CH$_3$ | OCH$_3$ | O | H | H | NO$_2$ | H | (60, CDCl$_3$) 1.25–1.6 (5H), 3.95 (3H), 4.15–4.4 (2H), 7.3 (2H), 8.15 (2H) |
| 11 | CH$_3$ | CH$_3$ | H | OC$_2$H$_5$ | O | Cl | H | Cl | Cl | (60, CDCl$_3$) 1.25 (3H), 1.4 (6H), 1.65 (1H), 4.0–4.6 (4H), 7.5 (1H) 7.6 (1H) |
| 12 | CH$_3$ | CH$_3$ | H | OCH$_3$ | O | Cl | H | Cl | H | (90, CDCl$_3$) 1.25 (3H), 1.35 (3H), 1.65 (1H), 3.9 (3H), 4.15–4.6 (2H), 7.2–7.55 (3H) |
| 13 | CH$_3$ | CH$_3$ | H | OC$_2$H$_5$ | O | NO$_2$ | H | H | H | (90, CDCl$_3$) 1.25 (3H), 1.35 (6H), 1.65 (1H), 4.2–4.65 (4H), 7.35 (1H), 7.65 (1H), 7.95 (1H) |
| 14 | CH$_3$ | CH$_3$ | H | OCH$_3$ | O | NO$_2$ | H | H | H | (60, CDCl$_3$) 1.2 (3H), 1.3 (3H), 1.6 (1H), 3.8 (3H), 4.2 (2H), 7.0–7.55 (3H), 7.8 (1H) |
| 15 | H | H | CH$_3$ | OCH$_3$ | O | NO$_2$ | H | H | H | (90, CDCl$_3$) 1.25–1.7 (5H), 3.95 (3H), 4.15–4.6 (2H), 7.35 (1H), 7.65 (1H), 8.0 (1H) |
| 16 | H | H | CH$_3$ | OCH$_3$ | O | Cl | H | Cl | Cl | (90, CDCl$_3$) 1.25–1.7 (5H), 3.95 (3H), 4.2–4.6 (2H), 7.55 (1H), 7.6 (1H) |
| 17 | CH$_3$ | CH$_3$ | H | OCH$_3$ | O | H | H | SCH$_3$ | H | (60, CDCl$_3$) 1.2 (3H), 1.3 (3H), 1.45–1.85 (1H), 2.4 (3H), 3.85 (3H), 4.3 (2H), 7.2 (4H) |
| 18 | CH$_3$ | CH$_3$ | H | OC$_2$H$_5$ | O | H | H | SCH$_3$ | H | (60, CDCl$_3$) 1.2 (3H), 1.3 (6H), 1.65 (1H), 2.4 (3H), 4.0–4.5 (4H), 7.2 (4H) |
| 19 | CH$_3$ | CH$_3$ | H | OC$_2$H$_5$ | O | H | CH$_3$ | SCH$_3$ | H | (60, CDCl$_3$) 1.2 (3H), 1.3 (6H), 1.65 (1H), 2.3 (3H), 2.35 (3H), 4.0–4.6 (4H), 7.1 (1H) |
| 20 | CH$_3$ | CH$_3$ | H | OCH$_3$ | O | H | CH$_3$ | SCH$_3$ | H | (60, CDCl$_3$) 1.2 (3H), 1.3 (3H), 1.6 (1H), 3.35 (3H), 3.4 (3H), 3.9 (3H), 4.3 (2H), 7.1 (3H) |
| 21 | H | H | CH$_3$ | OCH$_3$ | O | H | H | SCH$_3$ | H | (60, CDCl$_3$) 1.2–1.65 (5H), 2.45 (3H), |

-continued

Structure I: R¹R²C-C(Cl)(Cl)-CR³-CH₂-O-P(=Y)(R⁴)-O-C₆H(X¹)(X²)(X³)(X⁴)

| No. | R¹ | R² | R³ | R⁴ | Y | X¹ | X² | X³ | X⁴ | H—NMR data (MHz, solvent, δ-values) |
|---|---|---|---|---|---|---|---|---|---|---|
| 22 | H | H | CH₃ | OCH₃ | O | H | CH₃ | SCH₃ | H | (60, CDCl₃) 1.2–1.65 (5H), 2.3 (3H), 2.4 (3H), 3.9 (3H), 4.15–4.4 (2H), 7.2 (4H) |
| 23 | H | H | H | OCH₃ | O | H | H | CN | H | (60, CDCl₃) 1.2–2.3 (3H), 3.9 (3H), 4.1–4.4 (2H), 7.1 (3H) |
| 24 | H | H | H | OCH₃ | O | H | H | SCH₃ | H | (60, CDCl₃) 1.15–2.2 (3H), 2.4 (3H), 4.05–4.65 (2H), 7.35 (2H), 7.8 (2H) |
| 25 | H | H | H | OCH₃ | O | H | CH₃ | SCH₃ | H | (60, CDCl₃) 1.15–2.2 (3H), 2.3 (3H), 3.8 (3H), 4.0–4.5 (2H), 7.15 (4H) |
| 26 | H | H | H | OCH₃ | O | Cl | H | Cl | H | (60, CDCl₃) 1.2–2.5 (3H), 3.9 (3H), 2.4 (3H), 3.8 (3H), 4.0–4.5 (2H), 7.05 (3H) |
| 27 | H | H | H | OCH₃ | O | H | H | NO₂ | H | (60, CDCl₃) 1.2–2.5 (3H), 3.9 (3H), 4.1–4.6 (2H), 7.1–7.6 (3H) |
| 28 | H | CH₃ | H | OCH₃ | O | Cl | H | Cl | Cl | (60, CDCl₃) 1.15–1.9 (5H), 3.95 (3H), 4.15–4.65 (2H), 7.4 (2H), 8.2 (2H) |
| 29 | H | CH₃ | H | OCH₃ | O | Cl | H | Cl | H | (60, CDCl₃) 1.1–1.95 (5H), 3.95 (3H), 4.2–4.6 (2H), 7.7 (1H), 7.8 (1H) |
| 30 | H | CH₃ | H | OCH₃ | O | H | H | SCH₃ | H | (60, CDCl₃) 1.1–1.9 (5H), 2.45 (3H), 3.9 (3H), 4.15–4.6 (2H), 7.25 (4H) |
| 31 | H | CH₃ | H | OCH₃ | O | H | H | NO₂ | H | (60, CDCl₃) 1.1–2.0 (5H), 3.95 (3H), 4.15–4.65 (2H), 7.5 (2H), 8.35 (2H) |
| 32 | H | H | CH₃ | OCH₃ | O | Cl | H | NO₂ | H | (60, CDCl₃) 1.3–1.7 (5H), 4.0 (3H), 4.25–4.55 (2H), 7.7 (1H), 8.05–8.4 (2H) |
| 33 | H | H | CH₃ | OCH₃ | O | H | CH₃ | NO₂ | H | (60, CDCl₃) 1.3–1.7 (5H), 2.6 (3H), 3.9 (3H), 4.2–4.5 (2H), 7.1–7.4 (2H), 8.05 (1H) |
| 34 | H | H | CH₃ | OCH₃ | O | Cl | H | Br | H | (60, CDCl₃) 1.25–1.7 (5H), 3.95 (3H), 4.2–4.5 (2H), 7.4 (2H), 7.6 (1H) |
| 35 | H | H | CH₃ | N(CH₃)₂ | O | H | H | NO₂ | H | (60, CDCl₃) 1.3–1.65 (5H), 2.8 (3H), 3.0 (3H), 4.15–4.55 (2H), 7.6 (2H), 8.5 (2H) |
| 36 | H | H | CH₃ | N(CH₃)₂ | O | H | H | SCH₃ | H | (60, CDCl₃) 1.2–1.7 (5H), 2.5 (3H), 2.7 (3H), 2.9 (3H), 4.1–4.4 (2H), 7.4 (4H) |
| 37 | H | H | CH₃ | N(CH₃)₂ | O | Cl | H | Cl | H | (60, CDCl₃) 1.3–1.75 (5H), 2.75 (3H), 2.95 (3H), 4.2–4.5 (2H), 7.3–7.8 (3H) |
| 38 | H | H | CH₃ | NHCH(CH₃)₂ | O | NO₂ | H | H | H | (100, CDCl₃) 1.1–1.3 (6H), 1.3–1.6 (5H), 3.3–3.7 (2H), 4.0–4.45 (2H), 7.05–8.0 (4H) |
| 39 | H | H | CH₃ | NHCH(CH₃)₂ | O | H | H | NO₂ | H | (100, CDCl₃) 1.0–1.35 (6H), 1.35–1.6 (5H), 3.25–3.65 (2H), 3.95–4.4 (2H), 7.4 (2H), 8.2 (2H) |
| 40 | H | H | H | OCH₃ | S | H | H | NO₂ | H | (60, CDCl₃) 1.25–2.5 (3H), 4.05 (3H), 4.2–4.85 (2H), 7.6 (2H), 8.5 (2H) |
| 41 | H | H | H | OCH₃ | S | Cl | H | Br | H | (60, CDCl₃) 1.25–2.45 (3H), 4.05 (1H), 4.3–4.8 (2H), 7.55 (2H), 7.85 (1H) |
| 42 | H | H | H | OCH₃ | S | Cl | H | Cl | H | (60, CDCl₃) 1.25–2.55 (3H), 4.0 (3H), 4.3–4.85 (2H), 7.5 (2H), 7.6 (1H) |
| 43 | H | H | H | OCH₃ | S | H | H | SCH₃ | H | (60, CDCl₃) 1.25–2.5 (3H), 2.4 (3H), 4.05 (3H), 4.25–4.8 (2H), 7.2 (4H) |
| 44 | H | H | H | OCH₃ | S | H | CH₃ | NO₂ | H | (60, CDCl₃) 1.25–2.5 (3H), 2.7 (3H), 4.0 (3H), 4.2–4.8 (2H), 7.4 (2H), 8.3 (1H) |
| 45 | H | H | H | OCH₃ | S | NO₂ | H | H | H | (60, CDCl₃) 1.3–2.5 (3H), 4.05 (3H), 4.3–4.9 (2H), 7.4–7.95 (3H), 8.2 (1H) |
| 46 | CH₃ | CH₃ | H | OCH₃ | S | Cl | H | Cl | H | (60, CDCl₃) 1.25 (3H), 1.35 (3H), 1.7 (1H), 3.9 (3H), 4.35 (2H), 7.25 (2H), 7.4 (1H) |
| 47 | CH₃ | CH₃ | H | OCH₃ | S | H | H | SCH₃ | H | (60, CDCl₃) 1.3 (3H), 1.4 (3H), 1.7 (1H), 2.45 (3H), 3.9 (3H), 4.3 (2H), 7.2 (4H) |
| 48 | CH₃ | CH₃ | H | OCH₃ | S | H | H | NO₂ | H | (60, CDCl₃) 1.3 (3H), 1.4 (3H), 1.7 (1H), 3.9 (3H), 4.15–4.55 (2H), 7.4 (2H), 8.25 (2H) |
| 49 | CH₃ | CH₃ | H | OCH₃ | O | H | H | F | H | (60, CDCl₃) 1.25 (3H), 1.4 (3H), 1.7 (1H), 3.95 (3H), 4.4 (2H), 7.0–7.65 (4H) |
| 50 | CH₃ | CH₃ | H | S—i-C₄H₉ | O | Cl | H | Br | H | (60, CDCl₃) 1.0 (3H), 1.1 (3H), 1.3 (3H), 1.45 (3H), 1.5–2.5 (2H), 2.6–3.3 (2H), 4.2–4.85 (2H), 7.35–7.9 (3H) |
| 51 | CH₃ | CH₃ | H | NH₂ | O | Cl | H | Cl | H | (60, CDCl₃) 1.25 (3H), 1.4 (3H), 1.65 (1H), 3.3 (2H), 4.25 (2H), 7.45 (2H), 7.6 (1H) |

The following compounds of the formula VI may be prepared by the process described in Example 6:

$$\begin{array}{c} R^1 \\ R^2 \end{array}\!\!\!\!\bowtie\!\!\!\!\begin{array}{c} Cl \quad Cl \\ \\ R^3 \end{array}\!\!\!-CH_2-O-\overset{\overset{Y}{\|}}{\underset{Hal}{P}}-Hal$$

| R¹ | R² | R³ | Y | Hal | H—NMR data (MHz, solvent, δ-values) |
|---|---|---|---|---|---|
| CH₃ | CH₃ | H | S | Cl | (60, CDCl₃) 1.35 (3H), 1.5 (3H), 1.75 (1H), 4.1–4.8 (2H) |
| H | H | H | S | Cl | (60, CDCl₃) 1.3–2.6 (3H), 4.45–4.9 (2H) |
| CH₃ | CH₃ | H | O | Cl | (80, CDCl₃) 1.3 (3H), 1.45 (3H), 4.2–4.7 (2H) |
| H | H | CH₃ | S | Cl | (60, CDCl₃) 1.3–1.7 (5H), 4.45 (1H), 4.65 (1H) |

The following compounds of the formula III may be prepared by the process described in Examples 1 and 6:

$$\begin{array}{c} R^1 \\ R^2 \end{array}\!\!\!\!\bowtie\!\!\!\!\begin{array}{c} Cl \quad Cl \\ \\ R^3 \end{array}\!\!\!-CH_2-O-\overset{\overset{Y}{\|}}{\underset{R^4}{P}}-Hal \qquad III$$

| R¹ | R² | R³ | R⁴ | Y | Hal | H—NMR data (MHz, solvent, δ-values) |
|---|---|---|---|---|---|---|
| CH₃ | CH₃ | H | OCH₃ | O | Cl | (60, CDCl₃) 1.3 (3H), 1.45 (3H), 1.7 (1H), 3.9 (3H), 4.2–4.6 (2H) |
| H | H | CH₃ | N(CH₃)₂ | O | Cl | (60, CDCl₃) 1.3–1.65 (2H), 1.5 (3H), 2.65 (3H), 2.95 (3H), 4.15–4.7 (2H) |
| CH₃ | CH₃ | H | OCH₃ | S | Cl | (60, CDCl₃) 1.3 (3H), 1.4 (3H), 1.65 (1H), 3.85 (3H), 4.0–4.5 (2H) |
| CH₃ | H | H | OCH₃ | O | Cl | (60, CDCl₃) 1.2–1.8 (2H), 1.35 (3H), 3.9 (3H), 4.0–4.5 (2H) |
| CH₃ | CH₃ | H | S—n-C₃H₇ | O | Cl | (60, CDCl₃) 1.1 (3H), 1.35 (3H) 1.45 (3H), 1.5–2.2 (3H), 2.6–3.4 (2H), 4.2–4.85 (2H) |

The 2,2-dichlorocyclopropyl-methylphosphoric acid derivatives of the formula I according to the invention are suitable for effectively combating pests from the classes of insects, mites, ticks and nematodes. They may be employed for protecting crops and in the hygiene, stores protection and veterinary sectors.

Examples of these pests are insects from the Lepidoptera order, for example *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege stricticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus brovinus, Musca domestica, Fannia canicularis, Muscina stabulans, Glossina morsitans, Oestrus ocis, Chrysomya macellaria, Chrysomya hominivorax, Lucilia cuprina, Lucilia sericata* and *Hypoderma lineata;* examples from the Hymenoptera order are *Athalia rosae; Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilapravata lugens, Empoasca fabae, Psylla mali, Psylla piri, Trialeurodes vaporariorum, Aphis fabae, Aphis pomi, Aphis sambuci, Aphidula nasturtii, Cerosipha gossypii, sappaphis mali, Sappahis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes* and *Termes natalensis.*

Examples from the Orthoptera order are *Forficula auricularia, Acheta domestica, Gryllotalpa gryllotalpa, Tachycines asynamorus, Locusta migratoria, Siauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalene-sulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below:

I. 3 parts by weight of O-ethyl-O-[(2,2-dichloro-3,3-dimethylcyclopropyl)-methyl]-O-(4-nitrophenyl)-phosphate is intimately mixed with 97 parts by weight of particulate kaolin. A dust is obtained containing 3% by weight of the active ingredient.

II. 30 parts by weight of S-isobutyl-O-[(2,2-dichloro-3,3-dimethylcyclopropyl)-methyl]-O-(2-chloro-4-bromophenyl)-thiophosphate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of O-[(2,2-dichloro-1-methyl-cyclopropyl)-methyl]-O-(4-methylthiophenyl)-isopropyl-phosphoramidate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of O-[(2,2-dichlorocyclopropyl)-methyl]-O-(3-methyl-4-nitrophenyl)-thiophosphate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredients are applied in the form of these formulations or of ready-to-use preparations made therefrom.

The amount of active ingredient in the ready-to-use preparations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

There may be added to the individual active ingredients or mixtures thereof (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-]2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-0-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-0-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-0-[1-methyl-2-(methylcarbamoyl)-vinyl]-phosphate, O,O-dimethyl-0[(1-methyl-2-dimethylcarbamoyl)-vinyl]-phosphate, O,O-dimethyl-O[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethysulfynylethyl)-phosphorothioate, O,Odiethyl-S-(2-ethylthioethyl)-phosphorodithioate, O,O-diethyl-S-(2-ethylsulfynylethyl)-phosphorothioate, O,O-diethylthiophosphoryliminophenylacetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,-trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The biological action of the new compounds is illustrated in the following examples. Agents used for comparison purposes are the prior art active ingredients.

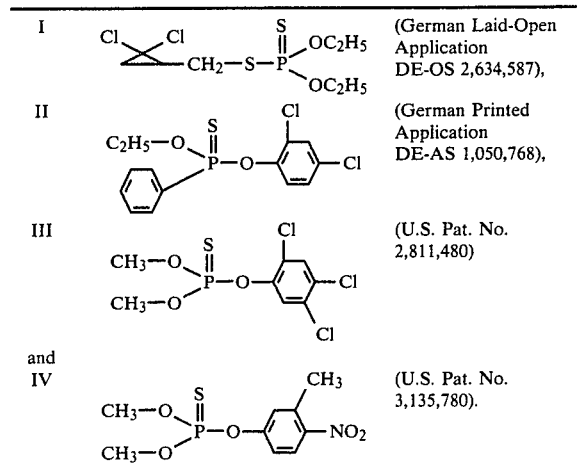

| | | |
|---|---|---|
| I | | (German Laid-Open Application DE-OS 2,634,587), |
| II | | (German Printed Application DE-AS 1,050,768), |
| III | | (U.S. Pat. No. 2,811,480) |
| and IV | | (U.S. Pat. No. 3,135,780). |

The other active ingredients are numbered as in the foregoing examples and the table.

EXAMPLE A

Contact action on cockroaches (*Blatta orientalis*)

The bottom of 1-liter preserving jars is treated with acetonic solutions of the active ingredients. After the solvent has evaporated, 5 adult cockroaches are placed in each jar, and the kill rate is determined after 48 hours.

| Active ingredient | Application of active ingredient per jar (mg) | Kill rate (%) |
|---|---|---|
| 1 | 0.25 | 80 |
| 7 | 0.2 | 100 |
| 10 | 0.04 | 100 |
| 21 | 0.1 | 100 |
| 23 | 0.1 | 100 |
| 24 | 0.1 | 100 |
| 25 | 0.2 | 100 |
| 27 | 0.02 | 80 |
| 31 | 0.2 | 100 |
| I | 5.0 | 100 |
| II | 1.0 | ineffective |
| III | 0.5 | 100 |
| IV | 0.25 | ineffective |

EXAMPLE B

Continuous contact action on houseflies (*Musca domestica*)

Both covers and bottoms of Petri dishes 10 cm in diameter are lined with a total per dish of 2 ml of acetonic solutions of the active ingredients. After the solvent has evaporated (about 30 mins.), 10 flies are introduced into each dish. The kill rate is determined after 4 hours.

| Active ingredient | Amount of active ingredient per dish (mg) | Kill rate (%) |
|---|---|---|
| 4 | 0.02 | 100 |
| 7 | 0.2 | 100 |
| 10 | 0.2 | 100 |
| 17 | 0.2 | 80 |
| 21 | 0.2 | 100 |
| 23 | 0.02 | 100 |
| 24 | 0.02 | 100 |
| 25 | 0.02 | 80 |
| 26 | 0.2 | 100 |
| 27 | 0.02 | 100 |
| 28 | 0.2 | 80 |
| 30 | 0.2 | 100 |
| 32 | 0.2 | 100 |
| 33 | 0.2 | 80 |
| I | 2.0 | 100 |
| II | 0.2 | ineffective |

EXAMPLE C

Contact action on houseflies (*Musca domestica*)

1 μl of the active ingredients dissolved in acetone is administered by means of a microsyringe to the ventral abdomen of 4-day old imagoes under slight $CO_2$ narcosis.

20 animals treated in the same way are then placed in a plastic bag having a volume of approx. 500 ml. After 4 hours, the animals in supine position are counted and the $LD_{50}$ is worked out by means of a graph.

| Active ingredient | $LD_{50}$ (μg/fly) |
|---|---|
| 4 | 0.055 |
| 23 | 0.073 |
| 24 | 0.051 |
| 27 | 0.057 |
| III | 0.13 |

EXAMPLE D

Contact action on bean aphids (*Aphis fabae*); spray experiment

Potted bean plants (Vicia faba) with extensive bean aphid colonies are sprayed to runoff in a spray booth with aqueous formulations of the active ingredients. The action is assessed after 48 hours.

| Active ingredient | Active ingredient concentration in formulation (wt %) | | Kill rate (%) |
|---|---|---|---|
| 1 | 0.02 | | 100 |
| 3 | 0.005 | | 100 |
| 4 | 0.01 | approx. | 90 |
| 7 | 0.01 | approx. | 90 |
| 10 | 0.01 | | 100 |
| 23 | 0.005 | approx. | 90 |
| 24 | 0.002 | | 100 |
| 25 | 0.005 | | 100 |
| 26 | 0.02 | | 100 |
| 27 | 0.005 | approx. | 90 |
| 28 | 0.02 | | 100 |
| 29 | 0.02 | | 100 |
| 30 | 0.01 | | 100 |
| 32 | 0.008 | | 100 |
| 33 | 0.01 | | 100 |
| I | 0.1 | | <50 |
| II | 0.02 | | <80 |

EXAMPLE E

Contact action and effect of ingested food on caterpillars of the diamondback moth (*Plutella maculipennis*)

Leaves of young cabbage plants are dipped for 3 seconds in aqueous emulsions of the active ingredients and, after excess liquid has been briefly allowed to drip off, placed on a moist filter paper in a Petri dish. 10 caterpillars of the 4th stage are then placed on each leaf. The action is assessed after 48 hours.

| Active ingredient | Active ingredient concentration in emulsion (wt %) | Kill rate (%) |
|---|---|---|
| 1 | 0.02 | 100 |
| 7 | 0.01 | 80 |
| 10 | 0.01 | 100 |
| 23 | 0.001 | 80 |
| 24 | 0.002 | 80 |
| 25 | 0.002 | 80 |
| 27 | 0.001 | 100 |
| 31 | 0.01 | 80 |
| I | 0.1 | 50 |
| III | 0.02 | 50 |

EXAMPLE F

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

| Active ingredient | Active ingredient concentration in emulsion (ppm) | Kill rate (%) |
|---|---|---|
| 1 | 10.0 | 100 |
| 4 | 5.0 | 100 |
| 7 | 10.0 | 100 |

EXAMPLE G

Action on root-knot nematodes (*Meloidogyne incognita*)

Garden soil heavily infested with *Meloidogyne incognita* is split into 200 g portions which are intimately mixed with 30 ml of aqueous active ingredient formulations and filled into plastic pots. Two cucumber seeds are then placed in the soil prepared in this manner. The temperature is not allowed to go below +22° C.

After 6 to 8 weeks root attack is assessed.

| Active ingredient | Active ingredient concentration (%) | |
|---|---|---|
| 16 | 0.05 | no root-knots |
| 17 | 0.1 | " |
| 30 | 0.1 | " |
| 36 | 0.1 | " |
| 40 | 0.1 | " |
| 47 | 0.1 | " |
| I | 0.1 | sporadic root-knots |

-continued

| Active ingredient | Active ingredient concentration in emulsion (ppm) | Kill rate (%) |
|---|---|---|
| 10 | 10.0 | 100 |
| 14 | 10.0 | 100 |
| 17 | 2.5 | 100 |
| 18 | 2.5 | 100 |
| 19 | 10.0 | 100 |
| 20 | 2.5 | 100 |
| 21 | 1.0 | 100 |
| 23 | 1.0 | 100 |
| 24 | 1.0 | 100 |
| 25 | 10.0 | 100 |
| 27 | 1.0 | 100 |
| 30 | 10.0 | 100 |
| 31 | 5.0 | 100 |
| 32 | 10.0 | 100 |

We claim:

1. 2,2-Dichlorocyclopropyl-methyl-phosphoric acid derivatives of the formula

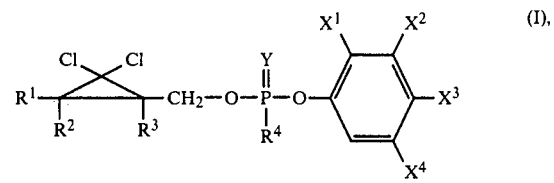

where
 $R^1$, $R^2$ and $R^3$ are identical or different and are hydrogen or methyl,
 $R^4$ is unbranched or branched alkoxy of up to 4 carbon atoms, unbranched or branched alkylthio of up to 4 carbon atoms, amino, or alkylamino or dialkylamino, wherein each alkyl is of up to 5 carbon atoms and is linear or branched,
 Y is oxygen or sulfur and
 $X_1$, $X_2$, $X_3$ and $X_4$ are identical or different and each is hydrogen, halogen, nitro, cyano, methyl or methylthio.

2. O-Methyl-O-[(2,2-dichloropropyl)-methyl]-O-(4-methylthiophenyl)-phosphate.

3. O-Methyl-O-[(2,2-dichlorocyclopropyl)-methyl]-O-(4nitrophenyl)-phosphate.

4. O-Methyl-O-[(2,2-dichlorocyclopropyl)-methyl]-O-(2-nitrophenyl)-thiophosphate.

5. A pesticide comprising a solid or liquid carrier and at least one 2,2-dichlorocyclopropyl-methyl-phosphoric acid derivative of the formula I as claimed in claim 1.

6. A process for combating pests, wherein an effective amount of a 2,2-dichlorocyclopropyl-methyl-phosphoric acid derivative of the formula I as claimed in claim 1 is allowed to act on the pests or their habitat.

* * * * *